United States Patent
Zhou (10) Patent No.: US 10,386,289 B2
(45) Date of Patent: Aug. 20, 2019

(54) METHOD AND SYSTEM FOR DETERMINING FEATURES OF OBJECTS IN A SUSPENSION

(71) Applicant: miDiagnostics NV, Leuven (BE)

(72) Inventor: Lin Zhou, Leuven (BE)

(73) Assignee: miDiagnostics NV, Leuven (BE)

(*) Notice: Subject to any disclaimer, the term of this patent is extended or adjusted under 35 U.S.C. 154(b) by 0 days.

(21) Appl. No.: 15/848,152

(22) Filed: Dec. 20, 2017

(65) Prior Publication Data

US 2018/0180527 A1 Jun. 28, 2018

(30) Foreign Application Priority Data

Dec. 23, 2016 (EP) .................................. 16206551

(51) Int. Cl.
| | | |
|---|---|---|
| *G01N 15/14* | (2006.01) | |
| *G06K 9/00* | (2006.01) | |
| *G03H 1/08* | (2006.01) | |
| *G03H 1/04* | (2006.01) | |

(52) U.S. Cl.
CPC ..... *G01N 15/1434* (2013.01); *G01N 15/1429* (2013.01); *G01N 15/1463* (2013.01); *G03H 1/0443* (2013.01); *G03H 1/0866* (2013.01); *G06K 9/0014* (2013.01); *G06K 9/00134* (2013.01); *G06K 9/00147* (2013.01); *G01N 15/1404* (2013.01); *G01N 2015/144* (2013.01); *G03H 2001/0447* (2013.01); *G03H 2001/0883* (2013.01)

(58) Field of Classification Search
CPC .......... G01N 15/1434; G01N 15/1404; G01N 2015/144
See application file for complete search history.

(56) References Cited

U.S. PATENT DOCUMENTS

| | | | |
|---|---|---|---|
| 8,660,312 B2 | 2/2014 | Cui et al. | |
| 2017/0284926 A1* | 10/2017 | Perraut | G01N 15/1475 |
| 2017/0363533 A1* | 12/2017 | Perraut | G01N 15/1434 |

FOREIGN PATENT DOCUMENTS

WO 2016019324 A2 2/2016

OTHER PUBLICATIONS

Kim et al., "Lens-Free Imaging for Biological Applications," Journal of Laboratory Automation, Jan. 2012, vol. 17, No. 1, pp. 43-49.

(Continued)

*Primary Examiner* — Jonathan M Hansen
(74) *Attorney, Agent, or Firm* — Hodgson Russ LLP (57) ABSTRACT

A method of directing a wavefront of coherent radiation through a sample of objects in a suspension, capturing an interference pattern between the wavefront of coherent radiation and a wavefront of the diffracted by the object with an image sensor, numerically determining the focal plane of at least one object, and numerically reconstructing a defocused image of the at least one object from the interference pattern in an image plane which is substantially parallel to the image sensor and in a plane with a predetermined offset from the focal plane. The method further includes identifying at least one portion in the defocused image corresponding to the at least one object in the sample, and calculating from each of said portions at least one feature of the corresponding object.

9 Claims, 5 Drawing Sheets

(56) References Cited

OTHER PUBLICATIONS

Wang et al., "Computational out-of-focus imaging increases the space-bandwidth product in lens-based coherent microscopy," Optica, Dec. 2016, vol. 3, No. 12, pp. 1422-1429.
McLeod et al., "Unconventional methods of imaging: computational microscopy and compact implementations," Reports on Progress in Physics, May 2016, vol. 79, No. 7, 30 pages.
EPO, Office Action for EP Application No. 17209504, dated Apr. 20, 2018.

* cited by examiner

METHOD AND SYSTEM FOR DETERMINING FEATURES OF OBJECTS IN A SUSPENSION

CROSS-REFERENCE TO RELATED APPLICATIONS

This application claims priority to European Application No. 16206551 titled "METHOD AND SYSTEM FOR DETERMINING FEATURES OF OBJECTS IN A SUSPENSION", filed Dec. 23, 2016, the entire disclosure of which is incorporated herein by reference in its entirety.

TECHNICAL FIELD

The description relates to a method and a system for determining features of objects in a suspension. More particularly, the description relates to a method and system for determining features of objects, such as small particles or cells, in a digital holography imaging arrangement.

BACKGROUND

Digital holography imaging has been used to simplify setups, for achieving a large field of view and eventually to avoid having a lens that may be expensive, sensitive to vibrations and has a need for alignment and re-alignment with the rest of the setup. Coherent light for illumination is traditionally used in digital holography imaging to get retraceable interference from the object or substance that is to be imaged. Light is diffracted by the illuminated object or substance and interferes with the reference light from the illumination source. This interference signal is captured by an image sensor. The sampled signal will not show an apparent image. The sampled signal, however, contains holographic information that may be used to numerically reconstruct an image plane corresponding to an image (in focus) produced with a lens system. The coherent light source may be naturally coherent as e.g. a laser or an incoherent light source combined with an aperture as e.g. an LED with a pin hole.

Digital holography may be performed with a lens for focusing purposes or done lens free. Lens free imaging has been used in biological applications for counting blood cells. A flow cytometer has traditionally been used as the standard diagnostics device for tests that rely on counting different types of blood cells. In a flow cytometer, a sample flows through a detection zone, typically one cell at a time, and cell properties are determined by an illumination and detection system. Using lens free imaging, a cheaper and more compact solution is achieved, suitable for lab on chip systems.

In one proposed system, a suspension with blood cells is guided through a flat channel on a chip. A light source illuminates the flow above the channel and an image sensor collect light underneath the channel. A simplified lens-free imaging technique without holographic reconstruction uses only the shadows of the cells passing the channel. This approach produces low quality image information compared to a holographic approach.

An alternative to this proposed solution would be to use a similar setup but with a traditional lens system. Focused images would then be obtained with more information than is available in the shadow images.

Other solutions are however known where digital holography imaging has been performed using holographic reconstruction to present an image corresponding to a focused image using a lens imaging system. These solutions are usually small and implemented on lab-on-chip systems. A problem with such systems has traditionally been that with a planar incident wave setup, the resolution in the reconstruction is insufficient to resolve the internal structure of the cells, making cell differential analysis a very challenging problem.

Another proposed system for counting particles in a suspension using digital holography imaging with a holographic approachuses a fiber optic cable as light source to resemble a light source with an aperture.

SUMMARY

According to a first aspect, there is provided a method for determining features of objects in a suspension, comprising: directing a wavefront of coherent radiation through a sample of objects in a suspension, capturing a pattern of interference between the wavefront of coherent radiation and a wavefront diffracted by the objects with an image sensor, determining the focal plane of at least one object where the object is in focus, numerically reconstructing a defocused image of the at least one object from the interference pattern in an image plane which is substantially parallel to the image sensor and in a plane with a predetermined offset from the focal plane, identifying at least one portion in the defocused image for each object corresponding to the at least one objects in the sample, and calculating from each of said portions at least one feature of the corresponding object.

According to a second aspect, there is provided a system for determining features of objects in a suspension, comprising: a coherent radiation source adapted for directing a wavefront of coherent radiation through a sample of objects in the suspension; an image sensor adapted for capturing a pattern of interference between the wavefront of coherent radiation and a wavefront diffracted by the objects; and a calculation unit adapted for receiving the captured pattern of interference; determining the focal plane of at least one object where the object is in focus; numerically reconstructing a defocused image of the at least one object from the interference pattern in an image plane which is substantially parallel to the image sensor and in a plane with a predetermined offset from the focal plane; identifying at least one portion in the defocused image for each object corresponding to the at least one object in the sample; and calculating from each of said portions at least one feature of the corresponding object.

According to a third aspect, there is provided a calculation device for identifying features of individual objects in a suspension comprising: a receiver adapted for receiving a pattern of interference between the wavefront of coherent radiation and a wavefront diffracted by the objects from an image sensor, and a calculation unit adapted for determining the focal plane of at least one object where the object is in focus, numerically reconstructing a defocused image of the at least one object from the interference pattern in an image plane which is substantially parallel to the image sensor and in a plane with a predetermined offset from the focal plane, identifying at least one portion in the defocused image for each object corresponding to the at least one object in the sample, and calculating from each of said portions at least one feature of the corresponding object.

According to a fourth aspect, there is provided a computer program product comprising computer program code means adapted for, in at least one image representing a pattern of interference between a wavefront of coherent radiation and a wavefront diffracted by at least one object, numerically reconstructing a defocused image of the at least one object from the interference pattern in an image plane with a predetermined offset from the focal plane where the object is in focus, identifying at least one portion in the defocused image for each object corresponding to the at least one object in the sample, and calculating from each of said portions at least one feature of the corresponding object, when said program is run on a computing device or means

BRIEF DESCRIPTION OF THE DRAWINGS

The above, as well as additional features and derived advantages, will be more fully appreciated by reference to the following illustrative and non-limiting detailed description of several embodiments described herein, when taken in conjunction with the accompanying drawings, wherein:

FIG. 1b illustrates a digital reconstruction of an image in a setup according to FIG. 1a.

FIG. 2b illustrates a digitally reconstructed image as a result of using a digital holography imaging arrangement as in FIG. 2a.

DETAILED DESCRIPTION

The present description provides an improved method and system for determining features of objects in a suspension. According to exemplary embodiments the provided solution is fast and/or cheap while still enabling a high enough resolution to be able to determine features of one or a large number of objects in a sample.

According to an example embodiment the method comprises directing a wavefront of coherent radiation through a sample of objects in a suspension, capturing an interference pattern of the wavefront of coherent radiation with an image sensor after it has been diffracted by objects in the sample when the wavefront passed through the sample, numerically determining the focal plane of at least one object (i.e. where the object is in focus), and numerically reconstructing a de-focused image of the at least one object from the interference pattern in an image plane which is substantially parallel to the image sensor and with a predetermined offset from the focal plane. The method further comprises identifying at one or more portions in the defocused image corresponding to one or more objects in the sample, and calculating, from each of said portions, at least one feature of the corresponding object.

The method, according to exemplary embodiments, is advantageously more tolerant for depth errors since the gradient in the image with respect to the reconstruction depth is less sensitive if the image is reconstructed in a de-focused manner rather than when in focus.

It is also advantageous that the boundary or contour of an object in a de-focused reconstructed image covers more pixels. Since more pixels with information are obtained for each object, the feature extraction can be simplified.

According to an example, the determination of the focal plane of an object may be performed by conventional auto focus algorithms or any other suitable method for finding a focal plane of an object.

According to an example, the predetermined offset of the reconstructed defocused image to the focal plane may be set below or equal to a threshold value, or maximum distance, at which individual objects may overlap in the image plane. In that way the spreading of the information over the image sensor pixels may be utilized to a maximum.

The step of identifying portions in the image corresponding to individual objects in the sample may further comprise detecting boundaries of the individual objects. The portions of the defocused image may be extracted by defining an image region containing all pixels of the object. That image region may be a fixed sized with a fixed shape for all the objects, for example, but not limited to: square, rectangular, circular. Extracting portions in the defocused image for each object makes it easier to perform image analysis of an individual object, since each individual object in the defocused image may then be treated on its own.

The at least one feature may further be a standard deviation of the pixel values or a normalized pixel values of a portion in the defocused image corresponding to an individual object. This may by itself, or in combination with another feature, be used to identify, differentiate and/or classify the types of objects.

The at least one feature may further be a mean of the pixel values or normalized pixel values of a portion in the defocused image corresponding to an individual object. This may by itself, or in combination with another feature, be used to identify, differentiate and/or classify the types of objects in the suspension.

The at least one feature may further be an area of the object in the defocused image corresponding to an individual object. This may by itself, or in combination with another feature, be used to differentiate different object types in the suspension or just determining object size.

The at least one feature may further be a contrast of the pixel values of a portion in the defocused image corresponding to an individual cell. This may by itself, or in combination with another feature, be used to differentiate different object types in the suspension.

The at least one object may in one embodiment be a cell in a suspension of cells. Different cell types may be differentiated by determination of the features mentioned.

The method may further comprise classifying cells based on the at least one calculated feature. The features may be used to determine which type of cells are present in a suspension by using one or a combination if the mentioned features.

The present description also includes a system for determining features of objects in a suspension. According to an example embodiment the system comprises a coherent radiation source adapted for directing a wavefront of coherent radiation through a sample of objects in the suspension, and an image sensor adapted for capturing a pattern of interference between the wavefront of coherent radiation and a wavefront diffracted by the objects. The system further comprises a calculation unit adapted for receiving the captured pattern of interference; determining the focal plane of at least one object where the object is in focus; numerically reconstructing a defocused image of the at least one object from the interference pattern in an image plane which is substantially parallel to the image sensor and in a plane with a predetermined offset from the focal plane; identifying at least one portion in the defocused image for each object corresponding to the at least one object in the sample; and calculating from each of said portions at least one feature of the corresponding object.

The present description also includes a calculation device for identifying features of individual cells in a suspension. The calculation device comprises a receiver for receiving a recorded signal of the interference pattern corresponding to a wavefront of coherent radiation that has traveled through and interfered with a sample of cells in a suspension. The calculation device further comprises a calculation unit adapted to numerically determine a focal plane of at least one object using the interference pattern, and numerically reconstructing a defocused image of the at least one object from the interference pattern in an image plane which is substantially parallel to the image sensor and in a plane with a predetermined offset from the focal plane. The calculation unit is further adapted to identify portions in the defocused image corresponding to individual objects in the sample, and calculate from each of said portions at least one feature of the corresponding individual cell.

The present description also includes a computer program product comprising computer program code means adapted for, in at least one image representing a pattern of interference between a wavefront of coherent radiation and a wavefront diffracted by at least one object, numerically reconstructing a defocused image of the at least one object from the interference pattern in an image plane with a predetermined offset from the focal plane where the object is in focus, identifying at least one portion in the defocused image for each object corresponding to the at least one object in the sample, and calculating from each of said portions at least one feature of the corresponding object, when said program is run on a computer.

The present description also includes a memory module comprising said computer program.

The present description also includes a system for identifying features of individual cells in a suspension, comprising a radiation source adapted to direct a wavefront of coherent radiation through a sample of objects in a suspension, an image sensor adapted to sense an interference pattern of the wavefront of coherent radiation after it has been diffracted by objects when passing through the sample, and a calculation device as described above. The calculation device is in communication with the image sensor for receiving an image of said sensed interference pattern.

The present description also includes a computing arrangement or mobile apparatus comprising the calculation device as previously described herein, the computer program product as previously described herein or the computer readable storage medium or storage unit previously described herein. The computing arrangement may e.g. be a computer, a server, a plurality of servers or a data center. The mobile apparatus may e.g. be a mobile phone, a tablet or any other portable computer device.

Figure 1A:
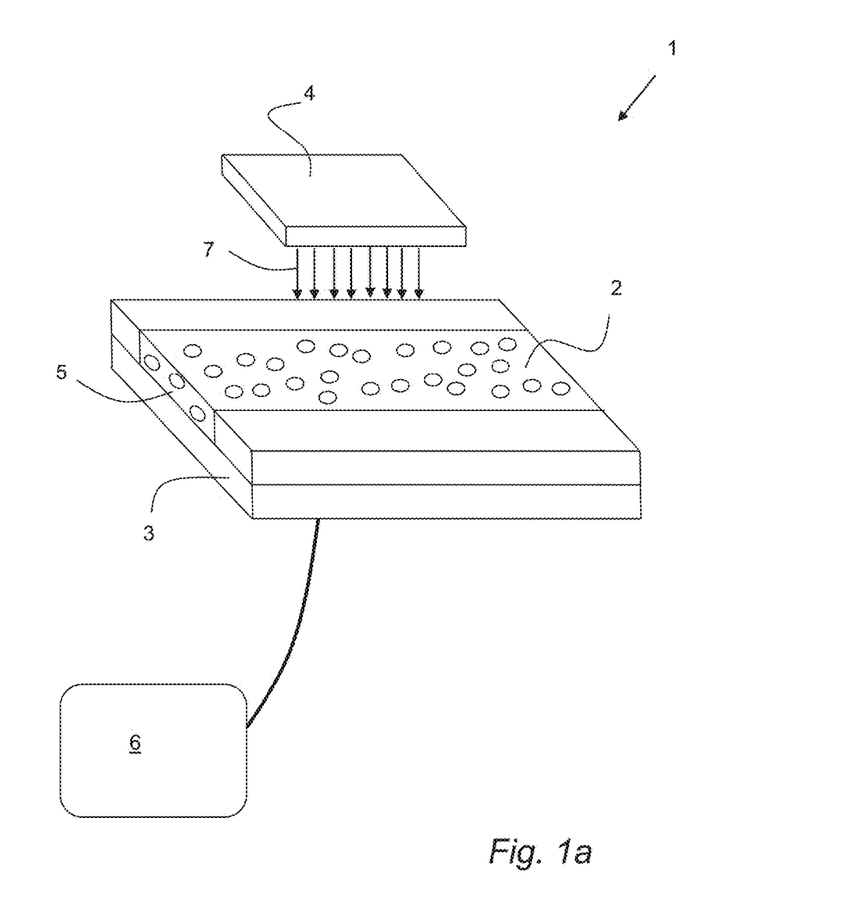
FIG. 1a shows a schematic view of a lens free digital holography imaging setup.

FIG. 1a is a schematic view of a lab on a chip lens free digital holography imaging setup 1. In use, a fluidic channel 5 is filled with a suspension 2 with objects and arranged on top of an image sensor 3. The channel 5 is irradiated with coherent light 7 from a light source 4. The light will be diffracted by the objects in the suspension. The diffracted light is interfered with the reference light 7, and the interference pattern is collected by the image sensor 3. The collected data is communicated to a calculation device 6.

The calculation device is configured to perform a method so as to reconstruct an image in an image plane from the holographic information contained in the interference pattern. The calculation device is further configured to perform a method for identifying features of individual cells.

Figure 1B:
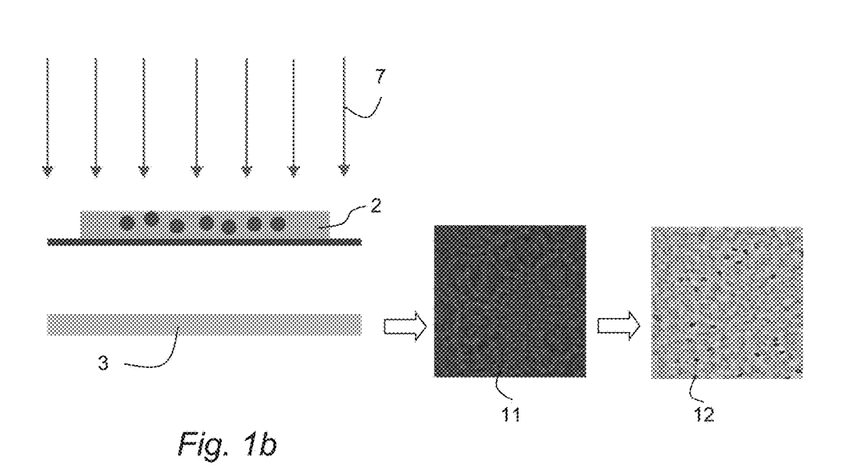

FIG. 1b is a schematic view of a digital reconstruction of an image using a setup as shown in FIG. 1. Coherent light 7 is irradiating a fluid suspension 2 containing objects, such as particles or cells. An image sensor 3 is recording the interference between the reference light 7 and the light that has been diffracted by the particles in the suspension. The raw data will produce an image 11 containing holographic information of the suspension and the particles therein. The holographic information is used to numerically reconstruct an image 12 of the suspension in an image plane where the particles in the suspension are in focus.

Figure 2A:
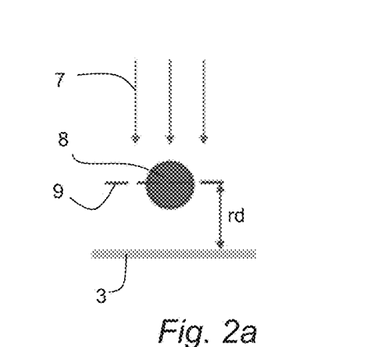
FIG. 2a shows a schematic view of a digital holography imaging arrangement.

FIG. 2a is a further schematic view of digital holography imaging arrangement. An image (as shown in FIG. 2b) is reconstructed at an image plane 9 where the particles in the suspension are in focus, with a reconstruction depth rd to the image sensor 3, that intersects the object 8.

Figure 2B:
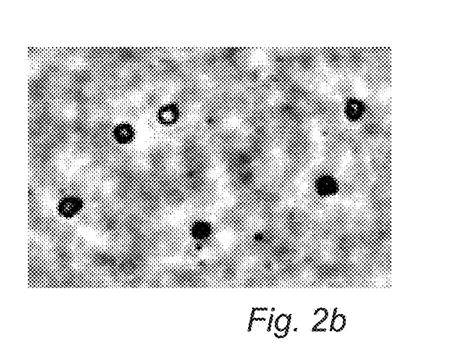

FIG. 2b shows a reconstructed image of a suspension containing blood cells where the numerically reconstructed image plane intersects the cells in accordance with the setup of FIG. 2a. The numerically reconstructed image is produced to make the image as sharp as possible. As seen in the image, the cells are sharp with clear edges.

Figure 3A:
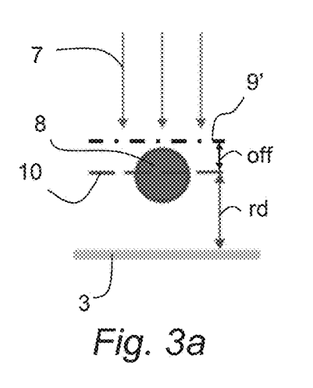
FIGS. 3a and 3b show a schematic view of de-focused digital holography imaging arrangements according to example embodiments.

FIG. 3a is a schematic view of a de-focused digital holography imaging arrangement according to a first exemplary embodiment. The reconstruction image plane 9' is now set in a plane not intersecting the object, corresponding to an image where the object is completely out of focus. The image plane 9' is placed with a certain offset (off) to a focal plane 10 of the object 8 (for example, a focal plane 10 through the middle of the object 8) to make sure that the image plane 9' is completely out of focus, i.e. not intersecting the object 8.

Figure 3B:
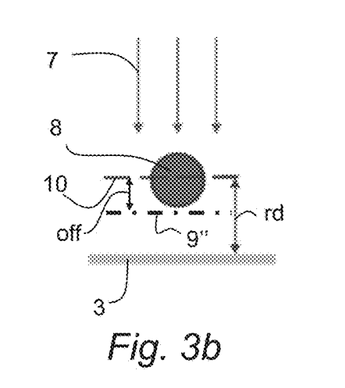

FIG. 3b is a schematic view of a de-focused digital holography imaging arrangement according to a second exemplary embodiment. In this example, the image plane 9" is placed with a certain offset (off) to a focal plane 10 of the object 8 (for example, a focal plane 10 through the middle of the object 8) along the opposite direction compared to the image plane 9' of the embodiment of FIG. 3a.

Figure 3C:
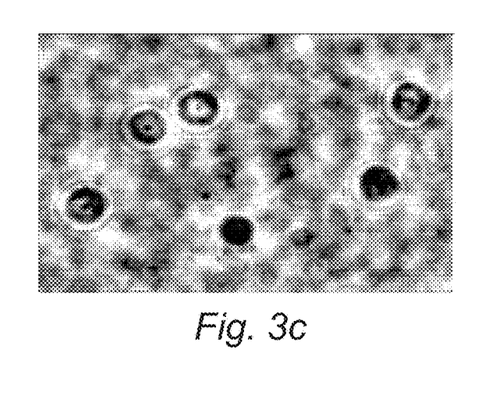
FIG. 3c is a digitally reconstructed image as a result of using a de-focused digital holography imaging method and system according to example embodiments.

FIG. 3c illustrates a reconstructed image using a defocused digital holography imaging arrangement, in which the reconstruction image plane 9' is offset by 38 μm to the image plane 9 of FIG. 2a. As can be seen, the cells in FIG. 3c are blurry compared to the cells in the image of FIG. 2b, where the reconstructed image plane intersects the cells or is in focus. The blurry cells of FIG. 3 also cover a greater area than the cells in the focused image of FIG. 2b, which will increase the area with valid information for each cell. Therefore, a de-focused digital holography imaging method, providing a reconstructed image that is reconstructed in a plane offset to a focused image plane, has the advantage that the measured signal for each individual cell will contain more information, since the de-focused image of a cell will cover more pixels on the image sensor.

According to an exemplary embodiment, the image from FIG. 2b, where an intersecting (focused) image plane is reconstructed, may be used as reference to determine the focal plane position and thereby determine a desired offset for a de-focused reconstructed image, but other ways of determining the focal plane 10 distance are possible.

De-focused digital holography imaging may be advantageously used for lab on chip systems which are miniaturized measurement systems for measurements on e.g. fluid suspension containing cells or particle objects where the cells or objects need to be detected, counted or diagnosed. The suspension could be, for example, urine, saliva, spinal fluid or blood. The image sensor may be only a few square millimeters in area and the fluid channel only a few millimeters wide. An image of a suspension with cells captured by the image sensor may contain thousands of individual cells.

Figure 4:
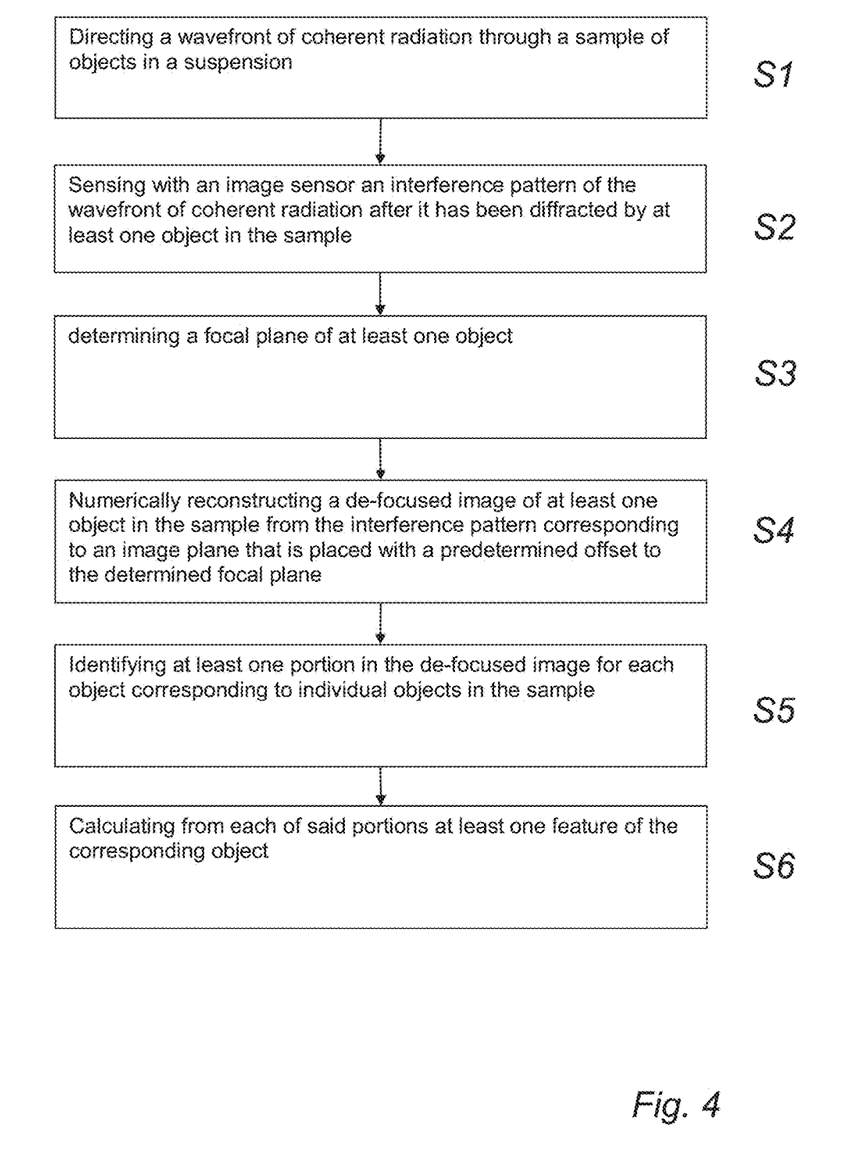
FIG. 4 shows a flow diagram of a method for determining features of objects in a suspension according to an example embodiment.

An example method of de-focused digital holography imaging according to the present description will now be described with reference to FIG. 4. In a first step S1, a light source is used to direct a wavefront of coherent radiation through a sample of objects in a suspension. The radiation may, for example, come from a laser that produces radiation that is coherent or be produced by a LED and a pinhole aperture arrangement which will produce a partly coherent radiation. The coherent radiation will be diffracted by the objects in the suspension. The diffracted light will interfere with the illumination radiation and create an interference pattern that contains holographic information with imaging information from all of each individual objects in the suspension.

In a second step S2, the interference pattern is sensed by an image sensor. The sensor is placed on the other side of the suspension compared to the light source so that the sensor will record the interference pattern of the diffracted light that has passed through the sample. The image sensor may be a small digital image sensor with an area of only a few square millimeters. According to an embodiment, the image sensor has a resolution high enough to resolve single particles in a suspension containing millions of particles.

In a third step S3 the interference pattern that is captured by the image sensor is used to determine a focal plane of at least one particle in the suspension using the holographic information in the interference pattern. This step may be performed using a conventional auto-focus algorithm.

In a fourth step S4, a de-focused image is reconstructed in an image plane parallel to the wavefront of the radiation and located with a predetermined offset (e.g. perpendicular) to the focal plane. The focal plane determined in the third step S3 is used as a reference to set the offset and thereby how much out of focus the defocused image is set.

In a fifth step S5, at least one portion of the image that corresponds to an object is identified. The at least one portion could e.g. be identified by finding boundaries or contours in the image that define the edges of the objects in the image. Finding the boundaries may be performed using image analysis algorithms for finding edges in images or similar image analysis techniques. The image may comprise a plurality of objects and this step may comprise identifying a plurality of image portions, each corresponding to a different object.

In a sixth step S6, a feature is determined from information in the at least one identified portion corresponding to an object or from information in each identified portion corresponding to each of the objects. The feature may be used to classify the object in the suspension in desired ways. The feature could be the size of the object, the standard deviation of the signal from the portion corresponding to an object, a mean value of the signal from the object, an area an object, and/or a contrast value for the image data for an object. The features could by themselves or in combination be used to classify object types, cell types, size distribution and so on to make quantitative measurements of the distribution and contents of objects, as e.g. cells, in a suspension. One way to differentiate different object types is to plot the features in a diagram or histogram and find clusters of objects in the plot. According to an example, a cluster may be mapped to an object type or size through a calibration process done on known samples.

The method for determining features of objects in a suspension may be performed in a calculation device or module, such as a computer, a mobile computer device, a mobile smart phone or an apparatus with a hardware and/or software configuration comprising a receiver for receiving a recorded signal of an interference pattern from a suspension of objects, and a calculation unit capable of performing logical steps in accordance with the method. The method can be realized by means of a number of commands written as a computer program, and said computer program may be stored on a memory and executed by the calculation device. The calculation device may form part of a system further comprising a radiation source to irradiate a sample of objects in a suspension with coherent radiation and an image sensor to record an interference pattern from the diffraction of the coherent light in the sample.

Figure 5:
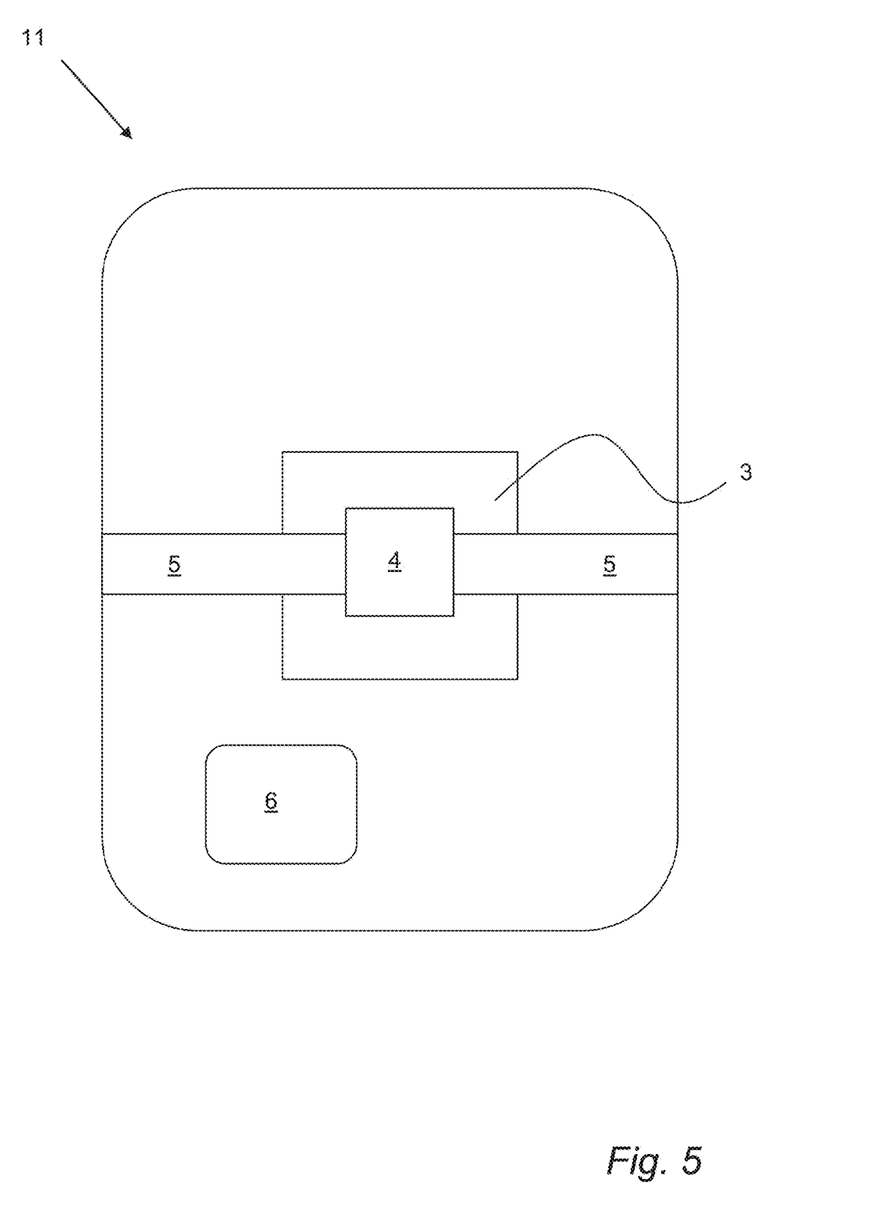
FIG. 5 shows a block diagram of a system for determining features of objects in a suspension according to an example embodiment.

FIG. 5 shows a schematic top view of a system 11 for determining features of objects in a suspension. A fluid channel 5, intended to be filled with a suspension with objects, is arranged on top of an image sensor 3. The channel 5 is irradiated with coherent light from a light source 4. When the channel 5 is filled with a suspension, the light from the light source 4 will be diffracted by the objects in the suspension. The diffracted light is then interfered with the illumination light from the light source 4, generating an interference pattern which will be subsequently collected by the image sensor 3. The collected data of the interference is communicated to a calculation device 6. The calculation device is configured to perform the method for determining features of objects in a suspension according to exemplary embodiment herein described.

The image sensor 3 may be, for example, an active pixel sensor, a charge-coupled device (CCD), a CMOS active pixel sensor, etc. The calculation device 6 may include a processor and a memory, which, which may be part of or separate from but in communication with, the processor. The memory can be, for example, a Random-Access Memory (RAM) (e.g., a dynamic RAM, a static RAM), a flash memory, a removable memory, and/or so forth. In some instances, instructions associated with performing the operations described herein (e.g., operate an image sensor, generate a reconstructed image) can be stored within the memory and/or a storage medium (which, in some embodiments, includes a database in which the instructions are stored) and the instructions are executed at the processor.

In some instances, the processor includes one or more modules and/or components. Each module/component executed by the processor can be any combination of hardware-based module/component (e.g., a field programmable gate array (FPGA), an application specific integrated circuit (ASIC), a digital signal processor (DSP)), software-based module (e.g., a module of computer code stored in the memory and/or in the database, and/or executed at the processor), and/or a combination of hardware- and software-based modules. Each module/component executed by the processor is capable of performing one or more specific functions/operations as described herein. In some instances, the modules/components included and executed in the processor can be, for example, a process, application, virtual machine, and/or some other hardware or software module/component. The processor can be any suitable processor configured to run and/or execute those modules/components. The processor can be any suitable processing device configured to run and/or execute a set of instructions or code. For example, the processor can be a general purpose processor, a central processing unit (CPU), an accelerated processing unit (APU), a field-programmable gate array (FPGA), an application specific integrated circuit (ASIC), a digital signal processor (DSP), and/or the like.

Some instances described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other instances described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, instances may be implemented using Java, python/C++, .NET, or other programming languages (e.g., object-oriented programming languages) and development tools. Additional examples of computer code include, but are not limited to, control signals, encrypted code, and compressed code.

What is claimed is:

1. A method for determining features of objects in a suspension, comprising:
    directing a wavefront of coherent radiation through a sample of objects in a suspension;
    capturing a pattern of interference, between the wavefront of coherent radiation and a wavefront diffracted by the objects, with an image sensor;
    determining the focal plane of at least one object where the object is in focus;
    numerically reconstructing an image of the at least one object from an interference pattern in an image plane which is substantially parallel to the image sensor and with a predetermined offset from the focal plane;
    identifying at least one portion in the image corresponding to the at least one object in the sample;
    calculating, from said at least one identified portion, at least one feature of the object; and
    classifying objects based on the at least one calculated feature.
2. The method according to claim 1 wherein the offset from the focal plane is selected so that the object in the reconstructed image covers more pixels than that object in a reconstructed image in the focal plane.
3. The method according to claim 1, wherein the offset from the focal plane is below a maximum distance at which individual reconstructed objects overlap in the image plane.
4. The method according to claim 1, wherein the step of identifying at least one portion in the image corresponding to the at least one object in the sample, comprises determining a portion around the at least one object.
5. A lens-free system for determining features of objects in a suspension, comprising:
    a coherent radiation source configured for directing a wavefront of coherent radiation through a sample of objects in the suspension;
    an image sensor configured for capturing a pattern of interference between the wavefront of coherent radiation and a wavefront diffracted by the objects; and
    a calculation unit configured to:
        receive the captured pattern of interference;
        determine a focal plane of at least one object where the object is in focus;
        numerically reconstruct a defocused image of the at least one object from the interference pattern in an image plane which is substantially parallel to the image sensor and with a predetermined offset from the focal plane;
        identify at least one portion in the defocused image for the at least one object in the sample; and
        calculate, from said at least one portion, at least one feature of the object, and classify objects based on the at least one calculated feature.
6. A calculation device for identifying features of individual objects in a suspension, comprising:
    a receiver configured for receiving a pattern of interference between the wavefront of coherent radiation and a wavefront diffracted by the objects in a sample from an image sensor, and
    a calculation unit configured to:
        determine a focal plane of at least one object where the object is in focus,
        numerically reconstructing a defocused image of the at least one object from the interference pattern in an image plane which is substantially parallel to the image sensor and with a predetermined offset from the focal plane,
        identify at least one portion in the defocused image for the at least one object in the sample, and
        calculate, from said at least one portion, at least one feature of the object, and classify objects based on the at least one calculated feature.
7. A non-transitory computer readable storage medium comprising a computer program product comprising computer program code adapted for, in at least one image:
    representing a pattern of interference between a wavefront of coherent radiation and a wavefront diffracted by at least one object in a sample,
    numerically reconstructing a defocused image of the at least one object from the interference pattern in an image plane with a predetermined offset from the focal plane where the object is in focus,
    identifying at least one portion in the defocused image for the at least one object in the sample, and
    calculating, from said at least one portion, at least one feature of the object, and
    classifying objects based on the at least one calculated feature, when said program is run on a computing device.

8. A computing arrangement or mobile apparatus comprising the calculation device according claim 6.

9. A computing arrangement or mobile apparatus comprising the non-transitory computer readable storage medium according to claim 7.

* * * * *